United States Patent [19]

Sauder

[11] 4,184,537

[45] Jan. 22, 1980

[54] SELECTIVE HEATING AND COOLING APPARATUS

[75] Inventor: James W. Sauder, San Ysidro, Calif.

[73] Assignee: Chattanooga Pharmacal Company, Chattanooga, Tenn.

[21] Appl. No.: 800,607

[22] Filed: May 26, 1977

Related U.S. Application Data

[63] Continuation-in-part of Ser. No. 616,909, Sep. 26, 1975, Pat. No. 4,026,299, and Ser. No. 728,262, Sep. 30, 1976.

[51] Int. Cl.² .............................................. F28F 7/00
[52] U.S. Cl. ..................................... 165/46; 62/324; 62/527; 128/400; 128/402; 165/29
[58] Field of Search ............. 128/400, 402; 62/324 A, 62/527, 196 B; 165/46, 29

[56] References Cited

U.S. PATENT DOCUMENTS

| | | | |
|---|---|---|---|
| 1,896,953 | 2/1933 | Hassell | 128/400 |
| 2,260,134 | 10/1941 | Ballman | 128/400 |
| 2,614,394 | 10/1952 | McGrath | 62/199 X |
| 2,726,658 | 12/1955 | Chessey | 128/400 |
| 3,257,819 | 6/1966 | Maloney | 62/199 |
| 3,734,810 | 5/1973 | Davis | 165/29 |
| 3,871,381 | 3/1975 | Roslonski | 128/400 |
| 3,916,911 | 11/1975 | Sauder et al. | 128/400 |
| 3,918,458 | 11/1975 | Nethery | 128/400 |
| 3,967,627 | 7/1976 | Brown | 128/400 |

FOREIGN PATENT DOCUMENTS

807612 1/1959 United Kingdom ................ 165/324 A

*Primary Examiner*—Albert W. Davis, Jr.
*Assistant Examiner*—Margaret A. Focarino
*Attorney, Agent, or Firm*—Bell, Seltzer, Park & Gibson

[57] ABSTRACT

An improved portable refrigeration apparatus for selectively cooling or heating a limb of a patient or the like, and which includes at least one flexible pad adapted to be wrapped around a bodily limb and which incorporates flexible tubing serving as an evaporator. A separate auxiliary evaporator is positioned downstream of the pad in the cooling mode to insure that all of the refrigerant is evaporated before returning to the compressor. A temperature control system is provided for the pad which, in the cooling mode, includes a by-pass conduit which by-passes the pad, and a temperature controlled valve for selectively opening and closing the by-pass conduit, and so that the refrigerant will flow concurrently through the by-pass conduit and the pad when the valve is opened. A reversing valve is provided for reversing the direction of flow of the refrigerant composition to effect heating of the pad, and in the heating mode, temperature control is accomplished by selectively actuating the reversing valve to switch to the cooling mode. In the preferred embodiment, there is also provided a by-pass pipe and a pressure actuated valve in the pipe, by which the refrigerant by-passes the pad during heating in the event the pressure in the pad becomes excessive. Also, where more than one pad is utilized, there is provided a check valve downstream of each pad during heating, with the valves acting to equalize the temperatures in the two pads during heating regardless of their respective elevations. Still further, the apparatus preferably includes two separate expansion valves, with one being operative in the cooling mode and the other being operative in the heating mode, to thereby permit different pressure settings in the two modes.

13 Claims, 3 Drawing Figures

SELECTIVE HEATING AND COOLING APPARATUS

BACKGROUND OF THE INVENTION

This application is a continuation-in-part of my co-pending applications Ser. Nos. 616,909, filed Sept. 26, 1975, now U.S. Pat. No. 4,026,299 and 728,262, filed Sept. 30, 1976.

In U.S. Pat. No. 3,916,911, there is disclosed a portable heating and cooling apparatus utilizing flexible pads to be wrapped around the limb or other body portion of a human or animal, for selectively heating or cooling that body portion. The portable apparatus is especially useful in treating sprains, strains or other muscular injuries to athletes or race horses, as soon after the injury occurs as possible in order to rapidly reduce swelling, fever or the like to the injured area. Such a device obviates the inconvenient use of ice packs for treating such injuries or muscular diseases or inflammation. In my earlier co-pending application Ser. No. 616,909, there is further disclosed an improvement of the patented device for both heating and cooling, selection being made by a reversing valve and utilizing at least one flexible pad and tubing and quick-connect couplings between the apparatus and the cooling and heating pads. That apparatus also includes a carrying case for the unit, one-way valve means for replenishing refrigerant composition in the unit, and an auxiliary heat exchanger for improving the efficiency of the apparatus.

In my later application Ser. No. 728,262, there is disclosed a cooling unit which include a by-pass pipe and thermostatically actuated valve means for selectively by-passing the pad and tubing so as to maintain a selected cold pad temperature. The present invention utilizes the by-pass concepts of the cooling apparatus application in a heating and cooling device and further includes means for maintaining selected pad temperature during heating regardless of the different pad elevations. These as well as other advantages, features, embodiments of the apparatus of the invention will be more fully explained hereinafter.

SUMMARY OF THE INVENTION

The apparatus of the present invention comprises a heating and cooling device utilizing refrigerant composition such as Freon (R-12) dichlorodifluoromethane and conduits for directing it through the various components including a compressor, condenser and fan, which condenser acts as an evaporator on heating, and a flexible pad and tubing which acts as an evaporator on cooling and a condenser on heating for being wrapped around an arm, leg or other desired body portion to be treated. The device also includes an auxiliary heat exchanger disposed along the refrigerant directing conduit system between the pad and compressor. A by-pass pipe intersects the conduit upstream from the pad for selectively directing the refrigerant to the auxiliary evaporator thereby by-passing the pad and tubing. The by-pass pipe is open and closed and by a thermostatically operated valve cooperating with temperature sensing means at the pad whereby the thermostat may be regulated by a suitable temperature selecting control means. Another important feature that may be incorporated is a positive pressure device comprising a supply line extending from the high side of the compressor to the auxiliary evaporator thereby by-passing the condenser, and an expansion valve or other pressure regulator means in the line for maintaining a selected refrigerant pressure in the system. Additionally, a hot gas by-pass pipe for the refrigerant composition during heating may be incorporated with a pressure actuated valve means to selectively open the pipe to by-pass the tubing and evaporator when pressure in the pad tubing is too high in a heating cycle. Further, two expansion valves are provided in the conduit system, one for directing refrigerant composition during heating and one during cooling are preferably used, and cooperate with a receiver for replenishing refrigerant composition in the apparatus. Additionally, check valves are used in the conduit system, and particularly a valve used for each cold inlet conduit to the pad and tubing which opens for refrigerant composition flow to the pads and tubing during cooling and which valves each have a small orifice therethrough for allowing a small amount of refrigerant composition to pass through the orifices during heating thereby obviating pad temperature differentials when the pads are at different elevations during the heating cycle. The specific details of these various components and embodiments as well as their interrelationship and advantages will be evident from the following detailed description.

DETAILED DESCRIPTION OF THE INVENTION

Figure 1:
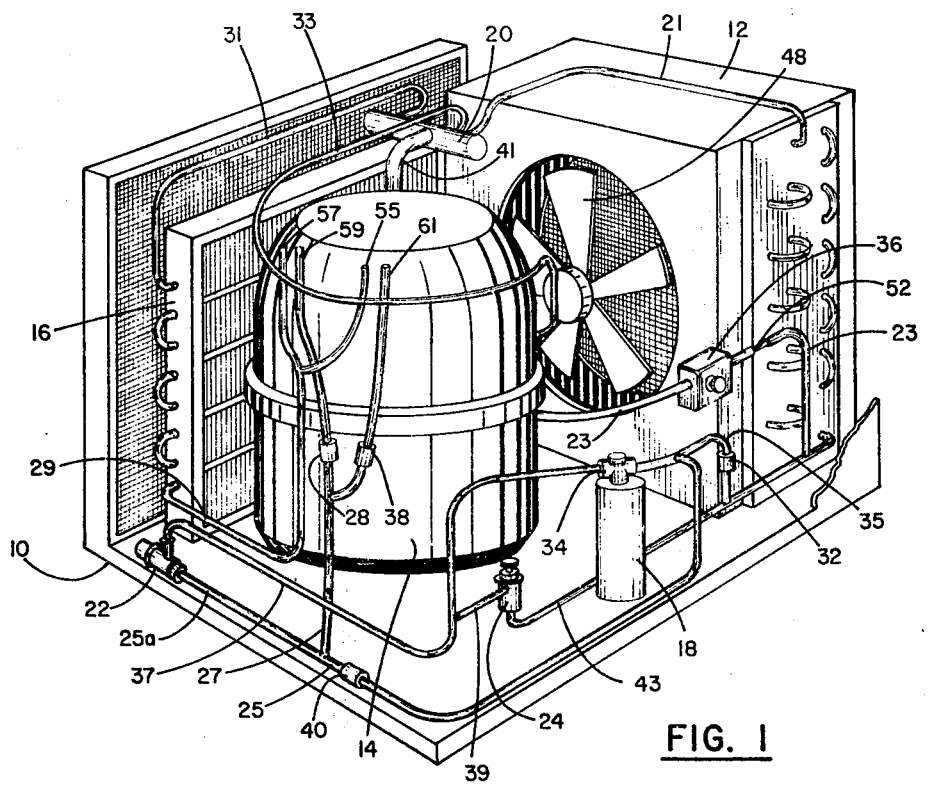
FIG. 1 is an illustration of the internal components of one embodiment of the apparatus of the invention showing the pressure actuated hot gas by-pass feature.
Figure 2:
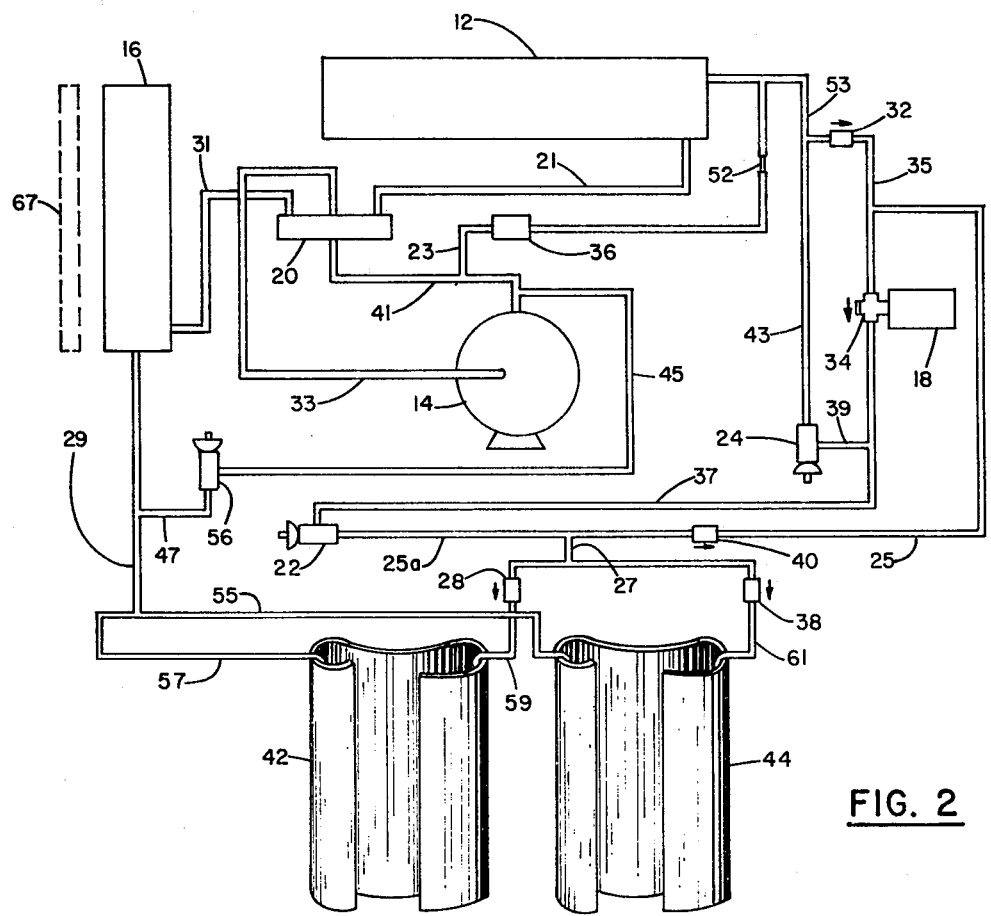
FIG. 2 is a schematic view illustrating the apparatus shown in FIG. 1 including flexible heating and cooling pads.
Figure 3:
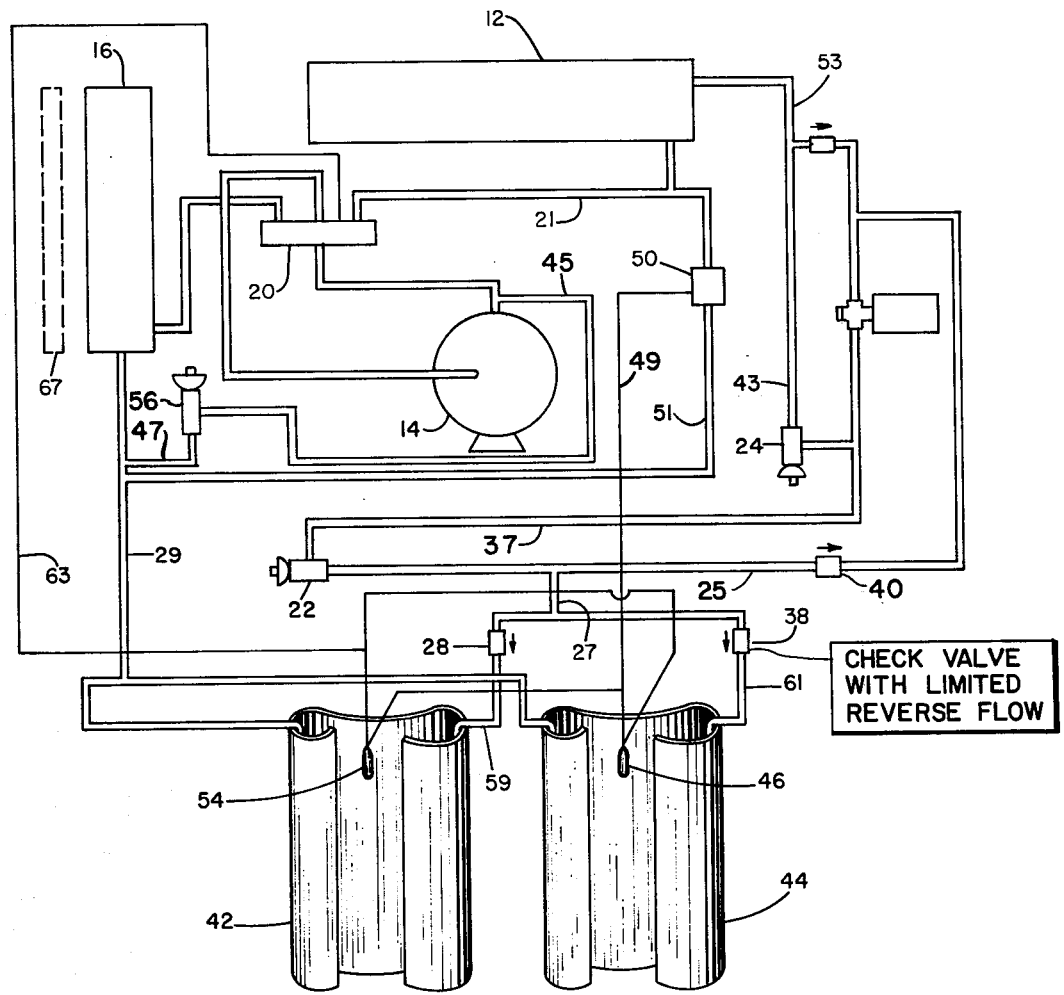
FIG. 3 is a schematic view illustrating alternative embodiments of the components of the apparatus including the thermostatically actuated by-pass feature.

FIGS. 1 and 2 illustrate the apparatus of the invention in the embodiment which does not utilize a system for maintaining automatic temperature control at the pad. However, the device is provided with a reversing valve for selecting heating or cooling of the pads as desired. In FIG. 3, there is illustrated a similar apparatus but having a thermostatically actuated by-pass means whereby the pads may be by-passed during cooling for maintaining a selected desired cold pad temperature. In the same embodiment, the temperature of the pads during heating may also be automatically regulated by thermostatically actuating the reversing valve. In the drawings illustrating either of these embodiments, the same components will be designated by the same numerals for ease of comparison.

Observing first FIG. 1 of the drawings, there is illustrated the apparatus generally which is enclosed in a case member 10, only a portion of which is shown. The preferred case is of the type illustrated in my co-pending application Ser. No. 616,909, and which case description is incorporated herein by reference. Moreover, the top of the apparatus will include a control panel as illustrated in both of my aforesaid co-pending applications and will include an on-off switching means, pressure sensing gauges, heating and cooling cycle selecting means and the like.

Major components of the apparatus include a condenser 12 and cooperating fan 48 for directing air past the condenser coils to condense refrigerant composition. The condenser acts as an evaporator during heating. Compressor 14 compresses refrigerant composition directed, via conduit 33, to its inlet or low pressure side. Auxiliary heat exchanger 16, which acts as an auxiliary evaporator during cooling and auxiliary condenser during heating includes a length of thermally conductive tubing, usually copper coils, for further increasing the efficiency of the apparatus as will be explained hereinafter further. Conduit 41 directs refrigerant composition from the compressor supply or high side to reversing valve 20 where it is further directed through the apparatus and components.

In the apparatus illustrated in FIGS. 1 and 2 which does not include automatic temperature control components, there are shown two pads 42 and 44. For each of the pads, a pair of conduits are used, one for refrigerant composition flow to the pads and tubing therein and the other for directing the refrigerant from the pads. Although two of the pads are shown, it will be understood that the apparatus may be modified to incorporate only one or more than two such pads in which case only one outlet and one inlet conduit will be required for the single pad or multiple inlets and outlets for more than two pads. The pads utilized are identical with those disclosed in both of my aforesaid co-pending applications, and the descriptions therein are incorporated herein by reference. Accordingly, the flexible pads will preferably be composed of an outside flexible insulating sheet, usually of a rubber composition, and a removably secured inside non-insulating sheet. Secured to the inside of the pads is a flexible hose or tubing for directing refrigerant composition within the pad. The pads are provided with straps or other means for securing them around a body portion to be treated utilizing the device.

Although not illustrated, conduits 55, 57, 59, and 61 which direct refrigerant composition to and from the pads, are secured to a top panel or plate of the apparatus utilizing quick-connect couplings to allow for easy connection or disconnection between the pads and the apparatus. Such couplings are disclosed in U.S. Pat. No. 2,823,048 and the use thereof in the present apparatus is disclosed in my aforesaid co-pending applications and which description is incorporated herein by reference.

HOT GAS BY-PASS

In operating a heating and cooling apparatus as described in U.S. Pat. No. 3,916,911 and my earlier aforesaid co-pending application, it has been found that pressure build-up in the pad tubing during heating may become higher than desired. Accordingly, in order to prevent possible damage to the tubing during extended heating cycle periods in which the apparatus is used, the present invention embodies the incorporation of a high pressure or hot gas by-pass means cooperating with a high pressure limit switch and valve. In FIGS. 1 and 2, conduit 23 communicates between conduits 41 and 53 on the high pressure side or supply end of compressor 14. Normally, during a heating cycle, refrigerant composition is directed from compressor 14 via conduit 41 through reversing valve 20 to conduit 31, into auxiliary condenser 16 and to the pads 42 and 44 via conduit 29 which splits into conduits 55 and 57. After leaving the pads and flexible tubing therein, refrigerant composition travels through conduits 59 and 61 respectively, through check valves 28 and 38, conduit 27 and 25 via check valve 40 to conduit 35. Thereafter, it travels through dryer 34 which is part of receiver 18 a reservoir for replenishing refrigerant composition in the system. From the dryer, composition passes via conduit 39 through expansion valve 24, conduit 43, conduit 53, through condenser 12, acting as an evaporator in this heating cycle, conduit 21, through reversing valve 20 and via conduit 33 into compressor 14. Valve 36 incorporates or cooperates with a high pressure limit switch set at or adjustable to a desired high pressure limit, for example, 180 p.s.i. Normally this pressure actuated valve 36 will be closed so that refrigerant composition will not be directed into conduit 23. Conduit 23 also includes a short portion of capillary tube 52 which thereby restricts the conduit and controls refrigerant flow.

This pressure actuated by-feature operates when pressure build-up in the system during heating exceeds or reaches the set pressure limit of the pressure limit switch, causing valve 36 to open. As this occurs, refrigerant composition will be directed from conduit 41 into conduit 23, through capillary tube 52, into conduit 53 and through evaporator 12, conduit 21 and returns to the compressor 14 via reversing valve 20 and conduit 33. Thus, refrigerant composition will continue to travel in that path thereby by-passing the auxiliary heat exchanger 16 and the pads until such time as the pressure has subsided whereupon valve 36 will close and the refrigerant will then return to travel in its normal path during the heating cycle as previously described. The capillary tube is preferably one of a relatively short length, for example, one-half to a few inches in length preferably about one inch. The internal diameter of the tube will preferably be between about 0.025 and 0.1 inch i.d. Preferably, the cap tube i.d. nominally be about 0.064 inch. This hot gas or high pressure by-pass is not illustrated in FIG. 3 for simplicity. However, it may also be incorporated in the automatic temperature maintaining device illustrated in FIG. 3 and described hereinafter.

PAD CHECK VALVES

As illustrated in FIGS. 1–3 one-way check valves 28 and 38 are located along conduits 59 and 61 respectively. These check valves are one-way valves and are open for refrigeration flow in the direction of the arrows. Accordingly, they are open when the apparatus is in a cooling mode in which refrigerant composition passes from expansion valve 22 to the pads via conduits 25a, 27, through the check valves and into conduits 59 and 61. Heretofore, with the use of two pads in a single apparatus as disclosed in my aforesaid patent and earlier co-pending application, when one of the pads is higher in elevation than the other during a heating cycle, the pad temperatures will be different. That temperature differential is obviously undesirable and it has been found that the pad most elevated will have the higher temperature. This problem is eliminated by incorporating the one-way check valves 28 and 38 along conduits 59 and 61, which are the outlet conduits for the pads during a heating cycle, and modifying these check valves with a small orifice through the check valve. By doing so, even though the valve is closed, refrigerant composition can flow through the orifice in the check valves in an opposite direction from the normal open valve flow. The size of the orifice will depend on the desired refrigerant flow but may be between about 0.010 and 0.10 inch and preferably nominally about 0.050 inch diameter. This small orifice in each of the check valves allows flow outwardly from conduits 59 and 61 to conduit 27 and on through the system as previously described during a heating cycle and controls refrigerant flow to prevent "loading" of one of the pads, i.e., unloads the pads evenly and at such a rate that pad temperatures will be substantially the same regardless of their respective elevations.

POSITIVE PRESSURE MEANS

In FIG. 2, there is illustrated the optional preferred means for maintaining a preselecting minimum pressure in the system so as to prevent possible vacuum in the flexible tubing at the pads during cooling. This feature is disclosed in my latter co-pending application Ser. No. 728,262 and which description is incorporated herein by reference, and is achieved by conduit 45 extending from conduit 41 on the high side or supply outlet of compressor 14. An expansion valve 56 or other pressure regulating valve means is located at the end of conduit 45 and passing therefrom is conduit 47 which intersects conduit 29 leading to auxiliary evaporator 16 in the cooling cycle or phase of operation of the apparatus. During normal cooling operation, composition passes from compressor 14 via conduit 41 to reversing valve 20, conduit 21 through condenser 12, conduit 53, through conduit 35 past one-way check valve 32 through dryer 34, conduit 37, expansion valve 22, conduit 25a, and into the pads and tubing via conduits 27, one-way check valves 28 and 38 and conduits 59 and 61. From the pads 42 and 44, the refrigerant composition will exit via conduits 55 and 57, conduit 29 through auxiliary evaporator 16, conduit 31, through reversing valve 20, out through conduit 33 whereupon it returns to compressor 14. It will be noted that check valves 32 and 40 allow passage of composition only in the direction of the arrows and the expansion valves are also one-way valves as is dryer/receiver 34 so as to prevent composition from being directed or otherwise passing through the apparatus contrary to that desired in order to achieve the proper functioning of the apparatus whether it be for cooling or heating as selected.

In order to maintain a desirable minimum pressure throughout this system during cooling, a positive pressure device is especially desirable in order to avoid possible vacuum in the cooling pad tube. Since this flexible tubing may consist of rubber or synthetic elastomer, which may be slightly porous, if a vacuum were to occur because of low refrigerant composition in the system, air could be entrained into the tubing and passed through the system which could cause contamination as well as damage to the compressor. In order to avoid this, a positive pressure device consists of the conduits 45, 47 and expansion valve 56 which valve may be manually adjusted for a desired minimum pressure. The expansion valve and conduits in this positive pressure means allows for refrigerant composition to by-pass condenser 12 and the pads whereby composition can pass directly from compressor outlet conduit 41 to auxiliary evaporator 16 via conduits 45,47 and 29 when the valve opens. Expansion valve 56 may be adjusted by an operator utilizing a manual adjustment knob on the end of the valve. When the pressure in the system falls to or below a selected minimum pressure to which the expansion valve has been adjusted, for example, 1-2 psi., it will cause the valve to open thereby directing all of the refrigerant composition to by-pass the pads and maintain the minimum preset pressure in the pads until refrigerant composition has been built up to exceed the minimum pressure. This minimum pad pressure is actually maintained by "artificially" pressurizing the pads because of a back pressure being created at the pads as refrigerant composition is directed into conduit 29 from the positive pressure expansion valve 42 and some refrigerant flow into the pads through the normal flow pattern. Moreover, although this positive pressure means is illustrated only with regards to FIG. 2, it should also be understood that it may be used in the apparatus illustrated in FIG. 3, if desired.

DOUBLE EXPANSION VALVES

In the embodiments illustrated in FIGS. 1-3, there are shown a pair of expansion valves 22 and 24 each being for a separate heating or cooling operation of the apparatus. The use of separate expansion valves, one for use in the heating cycle and the other during cooling, allows for setting different pressures of refrigerant composition in those different cycles and provides maximum cooling and heating capability without overloading the system. For example, if it was desired to achieve pad temperatures of 20° F. on cooling, and 110° F. heating, the expansion valves setting for the low temperature or cooling use would differ because of temperature-pressure relationships. Thus, a second expansion valve might be desired. The use of two such expansion valves and cooperating conduit for the two different heating and cooling cycles is used so that the changeover from hot to cold or vice versa may be done rapidly and without overloading or straining the apparatus and causing undue time delays when switching from hot to cold. Expansion valve 22 operates during the cooling cycle when refrigerant composition from condenser 12 passes via conduit 53, one-way check valve 32, conduit 35, dryer 34, conduit 37, through expansion valve 22 and into the pads and tubing via conduit 25a and 27, one-way check valves 28 and 38 which will be open to this direction, and conduits 59 and 61.

During a heating cycle, refrigerant composition is directed from the pads by conduits 59 and 61, through small orifices in check valves 28 and 38, conduit 27, through open check valve 40, conduit 25, conduit 35, through dryer 34, conduit 39, and through expansion valve 24 where it is directed to condenser 12 (acting as an evaporator) via conduits 43 and 53. Again, the cold temperature or cooling cycle expansion valve 22 will be set at a suitable valve pressure to achieve the desired minimum pad temperature whereas the heating cycle expansion valve 24 will be set or adjusted to meet the desired maximum high temperature requirements. Accordingly, with these two separate expansion valves being independently adjustable for respective heating and cooling cycles, the performance of the apparatus will be significantly improved. The two expansion valve embodiments will be used in both of the systems as shown in FIGS. 2 and 3.

THERMALLY ACTUATED BY-PASS

FIG. 3 illustrates an embodiment of the invention which provides for maintaining a preselected temperature at the pads during cooling and heating. The cooling and heating temperature maintenance means are independent of each other except that they both utilize temperature monitoring means at the pads. The means for maintaining pad temperatures during cooling is provided by by-pass pipe 51 which interconnects or extends between conduits 21 and 29 as illustrated. Solenoid valve 50 opens and closes the by-pass pipe in response to temperatures monitored at pads 42 and 44 by temperature sensing probes 54 and 46. When the thermally actuated solenoid valve 50 opens pipe 51, refrigerant composition passes through the pipe from conduit 21 to conduit 29 and into auxiliary evaporator 16. Accordingly, during the cooling mode of operation, when valve 50 opens by-pass pipe 51, condenser 12 and the pads and flexible tubing are by-passed and instead, refrigerant composition is simply directed to the auxiliary evaporator and circulates through the apparatus without further cooling the pad and flexible tubing. Actually, with by-pass pipe 51 open, as the major refrigerant flow is directed to conduit 29, and some refrigerant still flows to the pads this causes a back pressure in the pad and tubing thereby causing an increase in pad temperature until this back pressure condition is relieved when valve 50 again closes the by-pass pipe 51.

Where capillary tubes are used instead of the expansion valves 22 and 24, the by-pass pipe will communicate with conduit 53 rather than conduit 21 as shown in FIG. 3. Accordingly, in such an apparatus utilizing capillary tubes, the hot gas refrigerant will also pass through condenser 12 where it is cooled, and then into the by-pass pipe. This alternative is also explained and shown in my aforesaid co-pending application and that description is incorporated herein by reference.

Preferably, the valve cooperating with by-pass pipe 51 is responsive to a thermostat control. The thermostat control is provided by temperatures sensing probes 54 and 46 which are secured to the respective insulated pads so that the pad temperature is monitored and the by-pass pipe is automatically opened and closed in response to the monitored temperature. Preferably, a disconnecting plug along insulating conducting wire 49 is used so that the temperature sensors can be disconnected from the apparatus along with the pads in a manner as discussed in my latter co-pending application Ser. No. 728,262. In operation, the probes monitor temperature at the cooling pad and when the pad temperature is elevated past a selected temperature, valve 50 will close by-pass pipe 51 thereby preventing further by-pass of the refrigerant composition which then flows to the condenser and pads in the normal cooling operation. This cooling mode by-pass means is substantially like that discussed in my aforesaid prior co-pending application and any further description therein is incorporated herein by reference.

Temperature control, when the apparatus is utilized in the heating mode, is accomplished by alternately reversing the refrigerant composition flow utilizing reversing valve 20. Accordingly, as illustrated, temperature sensing probes 54 and 46 are electrically connected to a solenoid valve or similar means by insulated conductive wire 63 for actuating the reversing valve. This wire is also preferably provided with a disconnecting plug type arrangement as discussed regarding wire 49 and as disclosed in my prior co-pending application. The means for maintaining the pads at selected warm temperatures during heating, will thus involve a thermostatically actuated reversing valve 20 so that when pad temperature is elevated above a selected pad temperature, reversing valve 20 will be acutated which will thus cause the pads to be cooled, at which time the cooler temperature will be sensed and monitored by probes 54 and 46 which will then acutate the valve cooperating with reversing valve 20 to again apply heat at the pads.

It will be understood that these above disclosed means for maintaining pad temperature in the heating and cooling modes, are independent of each other. Accordingly, both or either one may be used on the same apparatus having these features and combined with a temperatue sensing means such as the probes as disclosed. Although probes 54 and 46 are shown as being secured at the pads whereby pad temperature would be monitored, it should be understood that the probes may instead be placed adjacent a patient's skin, for example, inserted between a cast and the patient's skin. The pad could then be wrapped around the cast and the probe would monitor the patient's skin temperature rather than the pad temperature so that the apparatus would continue to heat or cool until the desired skin temperature was achieved. Such an embodiment is further disclosed in my latter prior co-pending application Ser. No. 728,262. Moreover, the apparatus also preferably includes a temperature selecting scale on the apparatus control panel which may be indexed for desirable temperature ranges whereby operators may select a specific temperature within those ranges, whether for heating or cooling, and the apparatus will then maintain that temperature automatically utilizing these features. Moreover, the probes and a temperature control panel and selection means are disclosed in my prior co-pending application and those descriptions are incorporated herein by reference.

In a further optional embodiment, a heater 67 incorporating a resistive heating element may be used to supply heat to the auxiliary evaporator 16 to assist in heating refrigerant composition to insure that no liquid refrigerant passes on to foul the compressor during a cooling cycle operation. Such a feature may be particularly useful in cold weather outdoor operation or when the by-pass pipe is open during a cooling cycle use. The resistance heater may be electrically energized only during the cycle with the by-pass valve open. Further disclosure of such a heater are described in my aforesaid co-pending applications and are incorporated herein.

The apparatus of the invention is preferably enclosed in a case, such as a portable carrying case as is disclosed in the earlier aforsaid applications. Moreover, different size and shaped cooling pads may be used as may means for injecting make-up refrigerant composition in the disclosed apparatus as also described in my parent applications. Although the cooling pad may be used with flexible tubing, normally of a rubber or synthetic elastomer type, it is also within the scope of the invention to use any tubing which may be secured to the pads to be wrapped around a portion of the body to be treated. For example, a ductile copper tubing such as disclosed in the aforesaid patent may be used. These as well as other embodiments within the purview of the invention will be evident to those skilled in the art.

I claim:

1. A portable apparatus for selectively cooling or heating a limb of a patient or the like and comprising a compressor, a condenser, expansion valve means, at least one flexible pad adapted to be wrapped around a bodily limb and including flexible tubing serving as an evaporator, an auxiliary evaporator, conduit means including a reversing valve for selectively circulating a refrigerant composition
   (a) in a first cooling direction serially from said compressor to said condenser, to said expansion valve means, to said tubing, to said auxiliary evaporator and back to said compressor, and
   (b) in a second heating direction serially from said compressor to said auxiliary evaporator, to said tubing, to said expansion valve means, to said condenser, and back to said compressor, and a by-pass conduit operatively connected to said conduit means and extending from a point downstream of said compressor and upstream of said pad to a point downstream of said pad and upstream of said auxiliary evaporator when viewed in said cooling direction, and by-pass valve means for selectively opening and closing said by-pass conduit and so that the refrigerant composition will flow concurrently through the by-pass conduit and through the flexible tubing of said pad when said by-pass conduit is open and the refrigerant is circulating in said cooling direction, whereby the temperature of said pad during cooling may be controlled by the opening and closing of said by-pass valve means.

2. The apparatus as defined in claim 1 wherein said apparatus comprises a second like flexible pad operatively disposed in parallel with said one flexible pad in said conduit means, and each of said pads further includes an inlet tubing segment connected to one end of said flexible tubing for conducting the refrigerant composition into the associated pad during flow in the cooling direction and from the associated pad during flow in the heating direction, and check valve means disposed in each of said inlet tubing segments, said valve means being open to the flow of the refrigerant composition in said cooling direction while substantially restricting flow in said heating direction.

3. The apparatus as defined in claim 2 wherein each of said check valve means comprises a one-way valve having an orifice therethrough of between about 0.10 and 0.01 inches in diameter for restrictively permitting flow of the refrigerant composition in the heating direction.

4. The apparatus as defined in claim 1 wherein said expansion valve means comprises first and second expansion valves, and said conduit means further comprises means for conducting the refrigerant composition through only said first expansion valve during flow in said cooling direction, and through only said second expansion valve during flow in said heating direction.

5. The apparatus as defined in claim 1 wherein said by-pass conduit extends from a point downstream from said compressor and upstream from said condenser to said auxiliary evaporator when viewed in said cooling direction.

6. The apparatus as defined in claim 1 further comprising positive pressure means for maintaining a selected refrigerant composition minimum pressure in said tubing of said pad during cooling operation, said positive pressure means comprising a conduit line communicating with said conduit means at a point downstream from said compressor and upstream from said condenser and extending to a point immediately upstream of said auxiliary evaporator when viewed in said cooling direction, and pressure responsive valve means in said conduit line.

7. The apparatus as defined in claim 1 wherein said by-pass valve means includes means for monitoring the temperature at said pad, and means operable during cooling operation for closing said by-pass valve means when the temperature at the pad is above a pre-selected temperature, and for opening said by-pass valve means when the temperature at the pad is below a pre-selected temperature.

8. The apparatus as defined in claim 7 further comprising means operable during heating operation for actuating said reversing valve to cause said pad to be cooled when the temperature at the pad is above a pre-selected temperature, and for returning said reversing valve to its other position to cause said pad to be heated when the temperature at the pad is below a pre-selected temperature.

9. The apparatus as defined in claim 1 further comprising a resistive heating element positioned adjacent said auxiliary evaporator for supplying heat thereto during cooling operation.

10. The apparatus as defined in claim 1 further comprising a by-pass pipe operatively connected to said conduit means and extending from a point immediately downstream of said compressor to a point immediately upstream of said condenser when viewed in said heating direction, and a pressure actuated valve in said by-pass pipe for selectively opening said by-pass pipe during heating and upon the pressure of the refrigerant composition reaching a predetermined level.

11. A portable apparatus for selectively cooling or heating a plurality of limbs on one or a number of patients or the like, and characterized by substantially equal temperatures in each of the pads regardless of their respective elevations, and comprising: a compressor, a condenser, expansion valve means, evaporator means, and conduit means including a reversing valve for selectively circulating a refrigerant composition (a) in a first cooling direction serially from said compressor to said condenser, to said expansion valve means, to said evaporator means, and back to said compressor, and (b) in a second heating direction serially from said compressor to said evaporator means, to said expansion valve means, to said condenser, and back to said compressor, said evaporator means comprising at least two flexible pads, with each pad being adapted to be wrapped around a bodily limb and including flexible tubing serving as an evaporator, an inlet tubing segment connected to one end of said flexible tubing, and an outlet tubing segment connected to the other end of said flexible tubing, and means interconnecting said inlet and outlet tubing segments of all of said pads in parallel, and whereby the refrigerant flows into the pads through the inlet tubing segments during cooling and into the pads through the outlet tubing segments during heating, and check valve means disposed in each of said inlet tubing segments for permitting substantially unrestricted flow of the refrigerant in said cooling direction while substantially restricting flow in said heating direction.

12. The apparatus as defined in claim 11 wherein said evaporator means further comprises an auxiliary evaporator operatively connected to said conduit means and positioned downstream of all of said pads and upstream of said compressor when viewed in said cooling direction.

13. A portable apparatus for selectively cooling or heating a limb of a patient or the like and comprising a compressor, a condenser, expansion valve means, at least one flexible pad adapted to be wrapped around a bodily limb and including flexible tubing serving as an evaporator, an auxiliary evaporator, conduit means including a reversing valve for selectively circulating a refrigerant composition (a) in a first cooling direction serially from said compressor to said condenser, to said expansion valve means, to said tubing, to said auxiliary evaporator and back to said compressor, and (b) in a second heating direction serially from said compressor to said auxiliary evaporator, to said tubing, to said expansion valve means, to said condenser, and back to said compressor, and said expansion valve means comprising first and second separate expansion valves, and said conduit means further comprises means for conducting the refrigerant through only said first expansion valve during flow in said cooling direction, and through only said second expansion valve during flow in said heating direction.

* * * * *